United States Patent [19]

O'Reilly

[11] Patent Number: 4,735,201
[45] Date of Patent: Apr. 5, 1988

[54] OPTICAL FIBER WITH DETACHABLE METALLIC TIP FOR INTRAVASCULAR LASER COAGULATION OF ARTERIES, VEINS, ANEURYSMS, VASCULAR MALFORMATIONS AND ARTERIOVENOUS FISTULAS

[75] Inventor: Gerald V. O'Reilly, Swampscott, Mass.

[73] Assignee: The Beth Israel Hospital Association, Boston, Mass.

[21] Appl. No.: 824,075

[22] Filed: Jan. 30, 1986

[51] Int. Cl.⁴ .............................................. A61B 17/36
[52] U.S. Cl. .................................. 128/303.1; 128/325
[58] Field of Search .............. 128/303.1, 325, 395–398

[56] References Cited

U.S. PATENT DOCUMENTS

| 4,207,874 | 6/1980 | Choy | 128/6 |
| 4,519,390 | 5/1985 | Horne | 128/303 |
| 4,537,193 | 8/1985 | Tanner | 128/303 |
| 4,646,737 | 3/1987 | Hussein et al. | 128/303.1 |

FOREIGN PATENT DOCUMENTS 2826383  12/1979  Fed. Rep. of Germany ... 128/303.1

OTHER PUBLICATIONS

Gerald V. O'Reilly, M.D. et al., "Transcatheter Fiberoptic Laser Coagulation of Blood Vessels", Reprinted from Radiology, vol. 142, No. 3, pp. 777–780, Mar., 1982.

"Hot Tip": Another Method of Laser Vascular Recanalization, Abela et al., Lasers in Surgery and Medicine, 5:327–335, 1985.

Primary Examiner—Lee S. Cohen
Attorney, Agent, or Firm—Lorusso & Loud

[57] ABSTRACT

A device is described which includes an optical fiber or fiber bundle for transmission of laser energy with a proximal end for connection to a laser source and a distal end to which a heat generating tip or cap is securely, but detachably, affixed with a hot-melt adhesive. The heat generating tip serves to generate heat by absorption of laser energy for cauterization of tissue surrounding the neck of an aneurysm or other vascular opening to be occluded. The device is used for intravascular laser coagulation of arteries, veins, aneurysms, vascular malformations and arteriovenous fistulas. The heat generating tip of the device is positioned intravascularly within the neck of the aneurysm or other vascular opening to be occluded and laser energy is transmitted through the optical fiber to heat the tip and thereby coagulate the tissue surrounding the tip.

19 Claims, 1 Drawing Sheet

OPTICAL FIBER WITH DETACHABLE METALLIC TIP FOR INTRAVASCULAR LASER COAGULATION OF ARTERIES, VEINS, ANEURYSMS, VASCULAR MALFORMATIONS AND ARTERIOVENOUS FISTULAS

STATEMENT REGARDING FEDERALLY SPONSORED RESEARCH

The funding for work described herein was provided by the Federal Government, under a grant from the Department of Health and Human Services. The grant may have certain rights in the invention.

BACKGROUND OF THE INVENTION

1. Field of the Invention

The present invention relates to a method for intravascular laser coagulation of arteries, veins, aneurysms, vascular malformations and arteriovenous fistulas and to a catheter/optical fiber device for use with a laser in practicing the method.

2. Description of the Prior Art

The conventional treatment of conditions such as intracranial and other arterial aneurysms, arteriovenous fistulas, etc., involves major surgery and the use of clips or ties. For example, in the treatment of a ruptured intracranial aneurysm, a craniotomy is performed and the aneurysm neck is ligated. U.S. Pat. No. 4,360,023 to Sugita et al, U.S. Pat. No. 4,340,061 to Kees et al and U.S. Pat. No. 4,484,581 to Martin, for example, disclose various clips designed for sealing off the neck of an aneurysm. However, the unsuitability of certain patients for surgery and other logistical considerations often prevent this conventional surgical approach. In particular, in the case of patients who have suffered an aneurysmal subarachnoid hemorrhage and in patients exhibiting rebleeding after such a hemorrhage, the need exists for a safe and more expeditious treatment.

The prior art has also proposed various devices intended for precisely positioning intravascular occlusions as a therapeutic approach to the treatment of certain types of vascular disorders. For example, Handa et al in U.S. Pat. No. 4,346,712 disclose a balloon catheter for the embolization of vascular lesions. With the device of Handa et al, after inflation of a balloon to embolize the vascular lesion, the balloon is released from the tip of the catheter by heat.

Laser probes have been rather widely used for the cauterization of internal vessels, particularly in ophthalmic surgery. U.S. Pat. No. 4,537,193 to Tanner exemplifies a prior art disclosure of such a laser probe.

The prior art has also proposed the use of fiber optic laser catheters for use in various therapeutic procedures. See U.S. Pat. No. 4,519,390 issued to Horne and an article coauthored by the present inventor entitled "Transcatheter Fiber Optic Laser Coagulation of Blood Vessels," *Radiology*, Vol. 142, No. 3, pp. 777-780 (March 1982). That *Radiology* article reported the results of experimental work on rabbit ears which demonstrated that, with ues of a laser beam emanating from a flexible optical fiber within an artery, focal coagulation of the artery at a predetermined site was achieved in six out of ten experiments. The article suggested the possible application of such a technique in the treatment of a ruptured intracranial aneurysm. However, with such a technique, the potential exists for injury to other tissue in the vacinity of the target site, i.e. the neck of the aneurysm. The article also reviews various other prior art approaches to the treatment of aneurysms including the injection of foreign substances such as hairs and iron-acrylic material into the aneurysm and the intraluminal introduction of an inflatable balloon into the aneurysm cavity by means of a "superselective" catheterization of the cerebral arteries.

The use of fiber optic laser catheters has also been proposed for the recanalization of occluded vessels. Choy in U.S. Pat. No. 4,207,874 discloses such a catheter device which is intended to function by utilizing a laser beam to burn a hole through a thrombus occluding an internal vessel. However, again, such a technique presents the attendant problem of the potential for trauma to healthy tissue. Abela et al in "Hot Tip: Another Method of Laser Vascular Recanalization," *Lasers in Surgery and Medicine*, 5:327-335 (1985) propose use of a somewhat refined device for vascular recanalization. The device of Abela et al, like that of Choy, includes a laser, a catheter and fiber optics. However, the device of Abela et al further includes a metal cap on the distal end of the optical fiber which is heated by the laser energy. Thus, the device of Abela et al uses the heated metal tip, rather than a laser beam to burn through the thrombus and thereby avoids the potential problem of the laser beam damaging healthy tissue.

SUMMARY OF THE INVENTION

Accordingly, it is an object of the present invention to provide a method and apparatus for safely providing precisely positoned intravascular occlusions.

It is another object of the present invention to provide a method and apparatus for sealing off aneurysms, particularly, intracranial aneurysms, without major surgery.

Yet another object of the present invention is to provide a laser-catheter device and a method for using same to seal off aneurysms and other vascular lesions by cauterization without excessive tissue damage.

These and other objects and features of the present invention will become apparent to those skilled in the art from a reading of the ensuing description.

The apparatus of the present invention includes an optical fiber or fiber bundle for transmission of laser energy with a proximal end for connection to a laser source and a distal end to which a heat generating tip or cap is securely, but detachably, affixed with a hot-melt adhesive. The heat generating tip serves to generate heat by absorption of laser energy for cauterization of tissue surrounding the neck of an aneurysm or other vascular opening to be occluded. In its preferred embodiments, the apparatus of the invention includes a catheter providing a protective sheath around the optical fiber and, most preferably, the catheter is provided with a balloon located on or adjacent to its distal end and means for inflation of the balloon to cut off the flow of blood to the site to be cauterized and occluded.

In accordance with the method of the present invention, the heat generating tip is positioned intravascularly within the neck of the aneurysm or other vascular opening to be occluded and laser energy is transmitted through the optical fiber to heat the tip and thereby coagulate the tissue surrounding the tip. The heating of the tip also serves to melt the adhesive used to secure the tip to the distal end of the optical fiber, thereby allowing removal of the optical fiber from the vessel, leaving the tip in place and occluding the neck of the aneurysm or other vascular opening. The preferred method is to supply sufficient heat to coagulate the tissue surrounding the tip and, thereafter, allowing the coagulated tissue to set. After an appropriate setting time, laser energy is once again transmitted to the tip to melt the hot-melt adhesive, thus allowing withdrawal of the optical fiber. In the preferred embodiments using a balloon catheter, the balloon is inflated prior to cauterization to obstruct the flow of blood to the site to be occluded.

The invention find utility in any therapy requiring vascular coagulation and is particularly useful for the intravascular occlusion of:

intracranial or other arterial aneurysms;
internal arterial bleeding sites;
arteriovenous fistulas, e.g. carotid-cavernous, vertebral,
etc.;
arteriovenous malformations;
venous malformations;
arteries feeding vascular tumors;
damaged vessels following trauma; and
aortic dissection.

DESCRIPTION OF THE PREFERRED EMBODIMENT

Figure 1:
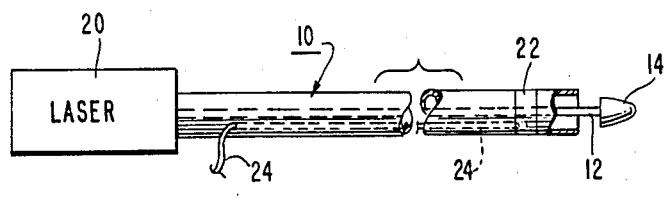
FIG. 1 is a schematic view, partially in cross-section, of one apparatus embodiment of the present invention.
Figure 3:
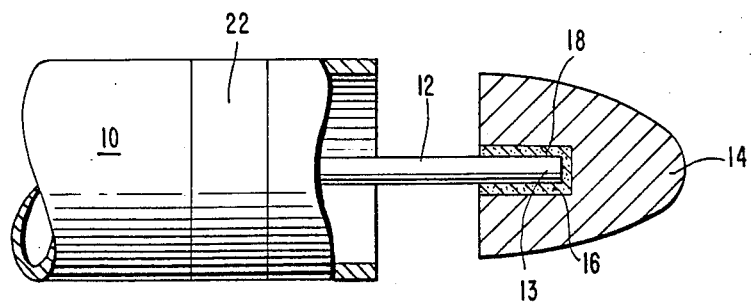
FIG. 3 is a side view, partially in cross-section, showing the detail of the tip of the apparatus of FIG. 1.

FIG. 1 illustrates a preferred embodiment of the apparatus of the present invention including a laser 20 and a catheter 10. The laser 20 is optically connected to an optical fiber 12 which extends through the lumen of catheter 10 to a point beyond the distal end of the catheter 10. As best illustrated in FIG. 3, a metallic tip 14, of a diameter slightly smaller than the inner diameter of catheter 10, is affixed to the distal end 13 of optical fiber 12 by means of a hot-melt adhesive 16. The metallic cap or tip 14 is preferably provided with a central bore 18 which receives the distal end of optical fiber 12 and the hot-melt adhesive 16.

Figure 2:
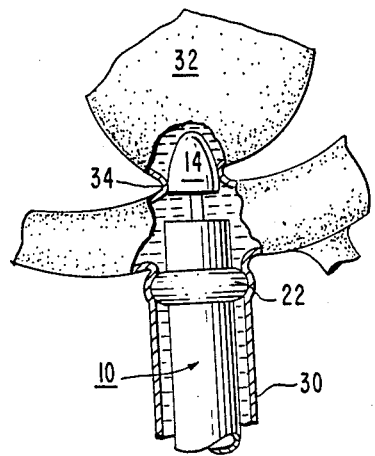
FIG. 2 is a schematic view, partially in cross-section, illustrating proper positioning of the apparatus of FIG. 1 for occlusion of an aneurysm.

The catheter 10 is preferably a balloon occluding catheter of the type conventionally used for angiography. Such balloon catheters are marketed, for example, by Cordis Corporation of Miami, Florida. As seen in FIGS. 1 and 2 of the drawings, the preferred embodiment illustrated there includes such a balloon catheter with the balloon shown in its uninflated state as a collar 22. As is conventional for balloon catheters, a passage 24 is provided within the catheter and in fluid communication with balloon 22 for supplying a fluid thereto for inflation.

Any non-magnetic, heat conductive and biocompatible material may be used for the cap or tip 14, such as silver or stainless steel. Silver is preferred because it is highly heat conductive, biocompatible and non-magnetic. The tip or cap 14 should also be radiopaque, which criterion is satisfied by any metal including silver which is the preferred material. The radiopaqueness of the tip allows the tip to be precisely positioned fluoroscopically within the neck of the aneurysm or other vascular opening to be occluded. Likewise, the catheter itself should be radiopaque to allow for positioning of its distal end preparatory to insertion of the tip 14 into the neck of the aneurysm or vascular malformation or lesion.

A plurality of cathater/optical fiber devices in accordance with the present invention, of different diameter, could advantageously be provided in kit form to allow for selection of a catheter and metal tip of size appropriate for occluding the particular aneurysm or lesion to be treated. In such a kit, the caps or tips 14 might vary in size, for example, from 0.5 mm to 1.0 mm. A typical catheter might have an inner diameter of 1 mm and an outer diameter of 1.5 mm. The dimensions are not particularly critical but should be such as to allow for free passage of the cap or tip 14 through the lumen of the catheter and the tip or cap 14 should be of a size approximating the size of the opening to be occluded.

In the preferred method of the present invention, the distal end of the catheter 10 is first positioned adjacent the neck of the aneurysm or the vascular malformation or lesion to be occluded using fluoroscopy or other method. As illustrated by way of example in FIG. 3, the optical fiber 12 is then extended through the lumen of the catheter until the cap 14 extends beyond the distal end of the catheter 10 and is positioned within the neck 34 of an aneurysm 32. Laser energy is then transmitted to the cap 14 for a period of time that will typically range from 15 seconds to 45 seconds to coagulate the tissue surrounding the cap 14. The coagulated tissue is then allowed to set, typically for a period of approximately one minute, and then laser energy is reapplied for a considerably shorter period of time than the first application, i.e. on the order of five seconds. This reheating of the cap 14 serves to again melt the adhesive 16, but upon this reheating the optical fiber 12 and catheter 10 are withdrawn leaving the cap 14 in place as a permanent plug.

EXPERIMENTAL

The experiments described below each utilized an argon laser (Innova 12, Coherent Inc., Palo Alto, Calif.) capable of delivering a maximum power of 12 W at wavelengths 457-514 nm (blue-green). The laser beam was transmitted through a shutter (Uni-Blitz 26 L, A. W. Vincent Associates,. Rochester, N.Y.) that controlled the duration of the exposure. Beyond the shutter a 2.5 cm diameter plano-convex lens (focal length 3 cm) was inserted to focus the beam onto the end of an optical fiber with a 100 $\mu$m diameter silica core and an acrylate buffer (Superguide G, Fiberguide Industries, Stirling, NJ). A small stainless-steel cylindrical cap 0.5 mm in diameter was firmly anchored to the distal end of the fiber with a hot melt glue. The fiber was aligned to the laser with a precision coupler (F-915, Newport Research Corp., Fountain Valley, Calif.). This was adjusted until maximum power transmission was obtained from the arterial end of the fiber, as measuared by an optical power meter (Model 210, Coherent Inc., Palo Alto, Calif.). The power output of the fiber was then altered to the desired level by monitoring the optical power meter while adjusting the laser power supply.

EXAMPLE 1

Six New Zealand white rabbits (4 kg) were anesthetized with intramuscular ketamine (35 mg/kg) and xylazine (5 mg/kg). In each animal the common carotid arteries were surgically exposed in the neck with the aid of an operating microscope. Systemic heparinization was instituted and a 5 cm segment of carotid artery isolated between temporary microvascular clamps. An arterial puncture was made with a 21-gauge needle about 1 cm distal to the proximal clamp. The optical fiber was introduced through the arteriotomy and advanced 3 cm into the carotid artery in a cranial direction. A termporary ligature of 4-0 silk was tightened around the carotid artery just distal to the arteriotomy to ensure no leakage of blood. The distal clamp was removed allowing blood to flow retrogradely to meet the fiber tip, though essentially the experiments were performed with interrupted blood flow.

Eleven lasings were performed at various power levels with exposure times dependent on the observed arterial effects. The endpoint of an exposure was determined when the wall of the artery at the fiber tip displayed discoloration and maximal focal contraction. On completion of the lasing, the 4-0 silk ligature was released. A second shorter exposure to laser energy resulted in detachment of the fiber from the steel cap and thereafter the optical fiber was effortlessly withdrawn from the artery.

Nine of eleven carotid arteries were focally coagulated with successful atraumatic detachment of the steel tip in all eleven arteries. In one of the coagulated arteries, after using the relatively low power of 450 mW for 15 seconds, the steel tip became dislodged. This occurred once arterial patency was reestablished at the arteriotomy site. It was determined from plain radiographs that the tip had embolized to the ipsilateral maxillary artery. In two cases the arteries at first showed minimal back-bleeding after fiber withdrawal. However, in each case, the bleeding ceased within 3 minutes, essentially resulting in an occluded vessel. The laser powers for complete coagulation ranged from 380-650 mW with exposure times of 10-40 seconds. 650 MW and 15 seconds appeared to be optimal for arterial coagulation. The steel tip detachment was effected by using the same power as for coagulation but with only a 5 second exposure. No arterial perforations occurred.

EXAMPLE 2

Four rabbits were anesthetized as in Example 1. In each animal the left femoral artery was surgically exposed in the groin. A 3.7-French radiopaque polyethylene catheter was introduced and manipulated under x-ray control into the origin of the right common carotid artery. Baseline carotid angiography was performed. An optical fiber system (coupled to an argon laser) as in Example 1, was advanced through the catheter until the fiber tip was fluoroscopically positioned in the carotid artery 4 cm beyond the catheter. Brief digital neck compression was applied over the carotid artery at the tip of the catheter so as to temporarily impede prograde arterial blood flow. 750 mW of laser power was administered through the fiber for a 15 second exposure during the digital carotid occlusion. Compression was immediately released and a small test injection of contrast medium performed to ascertain the status of the artery at the fiber tip. When the artery appeared focally occluded a second 5 second exposure of laser power was administered during which time the fiber was effortlessly withdrawn through the catheter leaving the steel cap detached in situ within the focal region of arterial coagulation. Control angiography was performed to document the arterial occlusion. The catheter was removed and the femoral artery and groin surgically closed.

EXAMPLE 3

Seven rabbits were anesthetized as in Example 1. Under sterile conditions with the aid of an operating microscope 10 experimental carotid aneurysms were surgically created. In each rabbit one or both carotid arteries were exposed in the neck. A vein pouch was omastomosed end to side with the common carotid artery using interrupted 10-0 monofilament nylon sutures.

Seven days after aneurysm production, the rabbits underwent transformal carotid angiography to establish continued aneurysm patency. Once established, an optical fiber system (coupled to an argon laser) as in Example 1, was advanced throught the catheter until the tip was fluoroscopically observed in the carotid artery. The ipsilateral carotid artery was surgically re-exposed in the neck to allow for direct observation of the experimental aneurysm. A temporary ligature of 3-0 silk was loosely positioned around the common carotid artery just proximal to the catheter tip. Under x-ray control and with confirmation by direct observation, the optical fiber system was advanced until its steel tip entered the neck of the aneurysm. The carotid ligature was tightened to impede prograde arterial flow and 750 mW of laser power administered through the fiber for a 15 second exposure. The ligature was then immediately released and a small test injection of contrast medium performed to fluorscopically ascertain the status of the aneurysm. When the aneurysm appeared occluded, a second 5 second exposure of laser power was administered during which the fiber was effortlessly withdrawn through the catheter leaving the steel cap detached in situ within the coagulated aneurysm neck.

Control angiography was performed to document the aneurysm occlusion. The catheter was removed and the femoral artery, groin and neck surgically closed.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. An optical fiber device for use in occluding a vessel, vascular malformation or vascular lesion, said device comprising:
   an optical fiber for transmission of laser energy;
   a detachable tip mounted with a hot-melt adhesive on one end of said optical fiber, said tip being absorptive of laser energy to produce heat and said hot-melt adhesive capable of being melted so that said detachable tip can be detached from said optical fiber and remain as an occlusion in the vessel.

2. The device of claim 1 wherein said tip has a bore into which said one end of said optical fiber is inserted and which contains said hot melt adhesive.

3. The device of claim 1 wherein said tip is a non-magnetic, biocompatible metal.

4. The device of claim 3 wherein said metal is silver or stainless steel.

5. The device of claim 1 wherein said tip is radiopaque.

6. A device in accordance with claim 1 further comprising a catheter serving as a sheath surrounding said optical fiber.

7. The device of claim 6 wherein said catheter comprises a distal end for positioning adjacent the point to be occluded, a balloon mounted on said catheter adjacent said distal end and means for inflation of said balloon.

8. The device of claim 6 wherein said catheter is radiopaque.

9. The device of claim 6 wherein said tip has a diameter less than the inner diameter of said catheter to allow for movement through the lumen of said catheter.

10. An apparatus for occlusion of a vessel, vascular malformation or vascular lesion, said apparatus comprising:
   a laser;
   optical fiber means having a proximal end and a distal end, said proximal end being optically connected to said laser for transmission of laser energy;
   a detachable tip mounted with a hot-melt adhesive on said distal end of said optical fiber means, said tip being absorptive of laser energy to produce heat and said hot-melt adhesive capable of being melted so that said detachable tip can be detached from said optical fiber and remain as an occlusion in the vessel; and
   a catheter forming a protective sheath around said optical fiber and having a central lumen, said lumen having a sufficient diameter to allow for free passage of said optical fiber means and said tip therethrough.

11. The apparatus of claim 10 wherein said tip and said catheter are radiopaque.

12. The apparatus of claim 10 wherein said catheter comprises a distal end, a balloon mounted on or adjacent said distal end and means for inflation or said balloon.

13. A method for occluding a vascular opening comprising:
   providing an optical fiber for transmission of laser energy and a detachable tip mounted with a hot-melt adhesive on one end of said optical fiber, said tip being absorptive of laser energy to produce heat and being of a diameter approximately the vascular opening to be occluded;
   positioning said tip within the vascular opening to be occluded;
   transmitting laser energy through said optical fiber to said tip to heat said tip thereby coagulating the tissue surrounding the opening and to fix said tip within said opening; and
   withdrawing said optical fiber from said tip, leaving said tip fixed within and occluding the vascular opening.

14. A method in accordance with claim 13 further comprising:
   discontinuing the heating of said tip for a period of time sufficient to allow the coagulated tissue to set; and
   again transmitting laser energy through said fiber to reheat said tip, thereby melting said hot-melt adhesive to allow withdrawal of said optical fiber.

15. The method of claim 13 wherein said vascular opening is the neck of an aneurysm.

16. A method in accordance with claim 15 wherein said aneurysm is a cerebral aneurysm.

17. A method in accordance with claim 13 wherein the distal end of a catheter is first inserted intravascularly to a point adjacent the vascular opening to be occluded and said optical fiber is then passed through the catheter until the tip extends beyond the distal end of the catheter and is located within the vascular opening to be occluded.

18. A method in accordance with claim 17 wherein said catheter is a balloon catheter and wherein said balloon is inflated to obstruct the flow of blood to the vascular opening to be occluded.

19. A method in accordance with claim 13 further comprising providing a plurality of said tips of different diameters and selecting a tip of a diameter approximately the size of the vascular opening to be occluded.

* * * * *